United States Patent [19]

Lohse et al.

[11] 4,288,565

[45] Sep. 8, 1981

[54] STORABLE, SOLID MIXTURE FOR THE PREPARATION OF PLASTICS WHICH ARE BASED ON EPOXIDE RESIN AND ARE STABLE TO HYDROLYSIS, THE USE OF THIS MIXTURE FOR THE PREPARATION OF SUCH PLASTICS AND PLASTICS OBTAINED IN THIS WAY

[75] Inventors: Friedrich Lohse, Oberwil; Ferdinand Gutekunst, Riehen; Rolf Schmid, Gelterkinden, all of Switzerland; Andre Schmitter, Hegenheim, France

[73] Assignee: Ciba-Geigy Corporation, Ardsley, N.Y.

[21] Appl. No.: 47,953

[22] Filed: Jun. 11, 1979

[30] Foreign Application Priority Data

Jun. 22, 1978 [CH] Switzerland .................. 6821/78

[51] Int. Cl.³ .................. C08L 63/00; C08L 61/06
[52] U.S. Cl. .................. 521/135; 525/481; 525/490; 525/524; 525/525; 525/526
[58] Field of Search .......... 525/524, 525, 526, 481, 525/490; 521/135

[56] References Cited

U.S. PATENT DOCUMENTS

| | | | |
|---|---|---|---|
| 2,801,989 | 8/1957 | Farnham | 260/47 |
| 3,275,708 | 9/1966 | Bylsign | 260/830 |
| 3,321,438 | 5/1967 | Brooker | 260/37 EP |
| 3,373,121 | 3/1968 | Bergart | 260/2.5 |
| 3,379,791 | 4/1968 | Larson | 525/525 |
| 3,383,433 | 5/1968 | Salensky | 260/831 |
| 3,484,398 | 12/1969 | Childs | 260/18 |
| 3,493,630 | 2/1970 | Salensky | 260/831 |
| 3,763,097 | 10/1973 | Edelman | 525/526 |
| 3,787,451 | 1/1974 | Mah | 525/524 |
| 3,862,260 | 1/1975 | Sellers | 260/831 |
| 3,884,992 | 5/1975 | Shimizu | 260/837 R |
| 3,950,451 | 4/1976 | Suzuki | 525/490 |
| 4,009,223 | 2/1977 | Noonan | 525/524 |
| 4,040,993 | 8/1977 | Elbling | 525/524 |
| 4,075,260 | 2/1978 | Tsen | 260/830 TW |

OTHER PUBLICATIONS

New Generation Hardener Designed for Powder Coatings; Dow Chemical Company, Midland Michigan, 3-7-75, pp. 1-12.

*Primary Examiner*—Paul Lieberman
*Attorney, Agent, or Firm*—Luther A. R. Hall

[57] ABSTRACT

Storable, solid mixture of (a) a long-chain epoxide resin which is free from ester groups and has a high epoxide equivalent weight, (b) an epoxide resin which is free from ester groups, contains cyclic structure and two to three epoxide groups in the molecule and has a low epoxide equivalent weight, (c) a triphenol and (d) a curing accelerator and, if desired, a blowing agent. Laminates, foams, compression moulded articles and adhesive bonds which are stable to hydrolysis, resistant to heat distortion and flexible are obtained on heating.

13 Claims, No Drawings

STORABLE, SOLID MIXTURE FOR THE PREPARATION OF PLASTICS WHICH ARE BASED ON EPOXIDE RESIN AND ARE STABLE TO HYDROLYSIS, THE USE OF THIS MIXTURE FOR THE PREPARATION OF SUCH PLASTICS AND PLASTICS OBTAINED IN THIS WAY

The invention relates to a storable, solid mixture which is used to prepare plastics which are based on epoxide resin and are stable to hydrolysis and which contains at least two different epoxide resins, a compound with at least 3 phenolic groups and a curing accelerator, and also to the use of this mixture for the preparation of plastics and to the plastics obtained in this way.

The reaction of tris-(glycidyloxyphenyl)-propane with polyhydric phenols in the presence of an alkaline catalyst is known from German Auslegeschrift No. 1,030,021. The mixtures can be compressed together with fillers under pressure and under the action of heat; they can also be used as impregnating resins for textile material. The reaction products form tough, hard resins. Their flexibility and/or their glass transition temperatures do not, however, always meet the desired requirements. The preparation of the glycidyloxy resins is also fairly expensive since large amounts of organic solvent have to be employed for this purpose and these have to be removed again.

The mixture according to the invention eliminates these disadvantages. It comprises (a) a long-chain, linear epoxide resin, which is free from ester groups, is solid at room temperature and has an epoxide equivalent weight of >700 and preferably >1,000, (b) a compound which is free from ester groups, contains cyclic structures and 2 or 3 epoxide groups in the molecule and has an epoxide equivalent weight of 100 to 400 and preferably 150 to 300, the components (a) and (b) being present in a ratio such that, per 1 total epoxide equivalent, 0.05 to 0.3 equivalent and preferably up to 0.2 equivalent originates from (a) and 0.7 to 0.95 equivalent and preferably 0.8 to 0.95 equivalent originates from (b), (c) at least one compound containing at least 3 phenol groups, in an amount such that there are 0.5 to 1.1 equivalents and preferably 0.9 to 1.0 equivalent of the phenolic hydroxy compound per epoxide equivalent, it being possible for up to 70 equivalent % of this compound to be replaced by phenolic bis-hydroxy compounds, and (d) a curing accelerator.

Compounds suitable as component (a) are, in particular, reaction products of n+1 mols of bisphenol A with n+2 mols of epichlorohydrin, n being a number from 2 to 15 and preferably 6 to 12, the said products being prepared in a manner known per se. Compounds suitable as component (b) are preferably diglycidyl ethers of bisphenol A and bis-phenol F, epoxyphenol novolacs or epoxycresol novolacs, triglycidyl isocyanurate or di- or triglycidyl derivatives of hydantoins. Examples of suitable hydantoins are N,N'-diglycidyl compounds of hydantoins substituted in the 5-position by lower alkyl groups, such as methyl or ethyl groups, or by a tetra- or penta-methylene group, or binuclear hydantoins which are glycidylated in the 1- or 3-position on the N atoms and in which the rings are bonded via the 3- or 1-position by a methylene group or by a 1,3-propylene group, which can be substituted in the 2-position by a lower alkyl group and/or a glycidyloxy group.

Compounds suitable as component (c) are preferably tris-(hydroxyphenyl)-propanes of the formula I

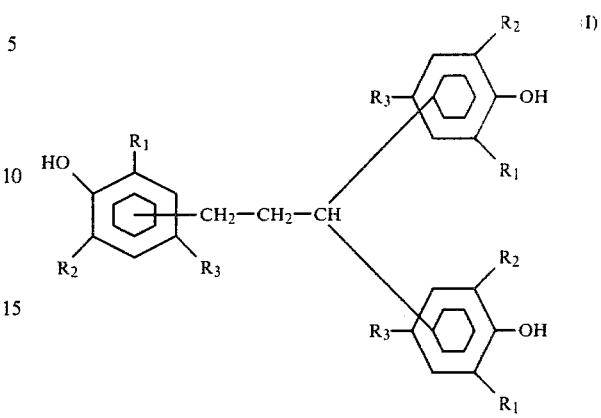

in which $R_1$ and $R_2$ independently of one another are hydrogen, methyl or halogen and $R_3$ is hydrogen or methyl. Preferably, $R_1$ and $R_2$ are hydrogen and $R_3$ is either hydrogen or methyl, or $R_1$ and $R_2$ are methyl or bromine and $R_3$ is hydrogen.

The preparation of these triphenols is described in German Auslegeschrift No. 1,030,021. With this procedure, in which 3 mols of a phenol are reacted in the presence of an acid catalyst with one mole of acrolein, higher polyphenols, pentaphenols and heptaphenols also form, in addition to the triphenols, when phenols having 2 or 3 active positions on the nucleus are used. A proportion of these triphenols, specifically up to 70 equivalent %, can be replaced by phenolic bis-hydroxy compounds. Suitable compounds of the latter type are the known bisphenols, such as bisphenol A and F and also mixtures of such bisphenols with halogenated bisphenols.

Compounds which can be used as component (d) for accelerating curing of the resin/curing agent mixture are tertiary amines, imidazoles, alkali metal alcoholates or quaternary ammonium salts, such as tetramethylammonium chloride.

The mixtures according to the invention can be prepared in a conventional manner, by, for example, mixing the resin and curing agent together at elevated temperature, for example at between 100° and 150° C., and, after cooling and comminuting, adding the curing accelerator. If it is intended to process the mixture immediately after it is prepared, the accelerator can also be admixed with the resin and the curing agent whilst the mixture is warm. The mixture has good flow characteristics when warm.

If a blowing agent is added, the compositions are also suitable for the preparation of foams.

The blowing agents added to the mixtures in order to prepare the foam are those which are still solid at room temperature and which have decomposition temperatures of between 80° and 220° C. These agents can be added on their own or as mixtures. Substances which can be used are sulfonyl hydrazides, for example benzenesulfonyl hydrazide, p-toluenesulfonyl hydrazide or 4,4'-oxydibenzenesulfonyl hydrazide, and also substances such as azodicarboxamides or α,α'-azoisobutyronitrile. Azodicarboxamide is preferably used as the blowing agent. The density of the novel foams is largely determined by the weight ratio of the reaction mixture to the blowing agent; this can vary from 0.1 to 1.0. Preferably, 0.5-7% of blowing agent are used.

In order to obtain a homogeneous pore structure, it is also possible to add a surfactant in amounts of 0.1% to 1%, based on the total amount of the reaction mixture. The mixture is usually poured into a mould, which can be closed if necessary. Foaming, shaping and curing take place in an oven, preferably at 160°-200° C., in the course of about ½ an hour to 6 hours. The foamed article formed can be taken from the mould if it is dimensionally stable at the temperature employed. If necessary, it can be post-cured at the same temperature or at a higher temperature, in order thus to obtain more advantageous properties in use.

The homogeneous mixtures which are stable on storage can be processed in the form of prepregs, sintering powders, moulding materials and powder adhesives, by heating to temperatures above 120° C. without a solvent, to give laminates, foams, compression moulded articles and adhesive bonds which have good hydrolysis resistance, heat distortion resistance and flexibility.

EXAMPLE 1

180 g (1.0 equivalent) of epoxide novolac with an epoxide content of 5.56 equivalents/kg, and 182 g (0.1 equivalent) of a diglycidyl ether of so-called "advanced" bisphenol A, prepared, for example, from about 6 mols of the diglycidyl ether of bisphenol A and 5 mols of bisphenol A in the presence of tetraammonium chloride, with an epoxide content of 0.55 equivalent/kg are mixed at 140° C. with 57 g (0.5 equivalent) of bisphenol A and 48 g (0.5 equivalent) of 1,1,3-tris-(hydroxyphenyl)-propane, i.e. a compound of the formula I in which $R_1=R_2=R_3=$hydrogen. 0.93 g (0.2%) of 1-methylimidazole is then mixed in and the mixture is poured immediately onto a cold Al sheet. The resulting product is grindable and has the following characteristics:

| | |
|---|---|
| Glass transition temperature (DSC-1, 16° C./minute) | = 48° C. |
| Gel time at 160° C. | = 180 seconds |

After curing the mixture, the following bond strengths under torsion on aluminium are measured:

| | |
|---|---|
| Curing for 30 minutes at 160° C. | = 76 N/mm² |
| Curing for 2 hours at 140° C. and 2 hours at 210° C. | = 82 N/mm². |

Preparation of 1,1,3-tris-(hydroxyphenyl)-propane 0.9 ml of 33% by weight hydrochloric acid is added to 1,410 g (15 mols) of phenol and the mixture is heated to 45° to 55° C. After this temperature has been reached, 56 g (1 mol) of acrolein are added dropwise and a slightly exothermic reaction takes place. The temperature is kept at a maximum of 65° C. by ice-cooling. After 10 minutes, all the acrolein has been added and the reaction mixture is then stirred for a further 1 hour at 100° C. The phenol which has not reacted is then distilled off under a waterpump vacuum. For this purpose, the temperature must be raised continuously until, after about 3 hours, at 200° C. no further distillate passes over. The residue solidifies at room temperature to a pale red-brown glassy mass. The softening range is from 40° to 50° C.

Evaluation of the analysis by gel chromatography shows that the product is a mixture of at least 3 components, the proportion of tris-(hydroxyphenyl)-propane being 68% by weight.

The product also contains 20% by weight of pentaphenol and 10% by weight of heptaphenol in addition to small proportions of higher molecular weight products.

The following structural formulae can be assigned to the polyphenols:

Trisphenol:

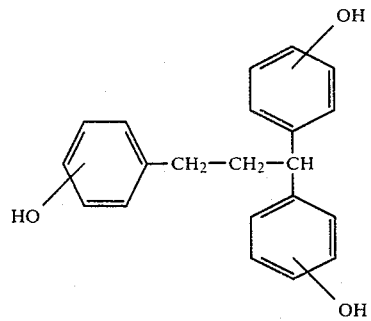

Pentaphenol:

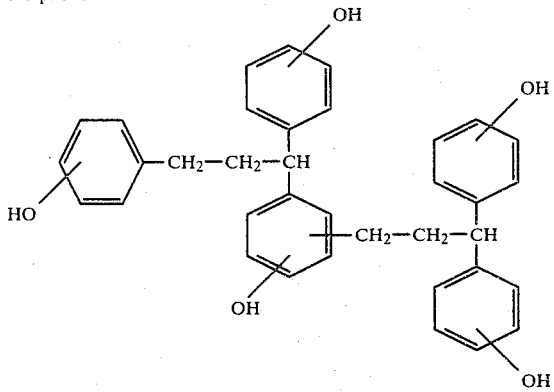

EXAMPLE 2

182 g (0.1 equivalent) of a diglycidyl ether of so-called "advanced" bisphenol A, prepared, for example, as indicated in Example 1, with an epoxide content of 0.55 equivalent/kg, and 167 g (0.9 equivalent) f a diglycidyl ether of bisphenol A with an epoxide content of 5.4 equivalents/kg are mixed, at 140° C., with 96 g (0.9 equivalent) of the trihydroxy compound of the formula I in which $R_1=R_2=R_3=$hydrogen. 0.34 g (0.1%) of 1-methylimidazole is mixed in and the mixture is then immediately poured out onto a cold Al sheet. The resulting product is grindable and has the following characteristics:

| | |
|---|---|
| Glass transition temperature (DSC-1, 16° C./minute) | = 39° C. |
| Gel time at 160° C. before storage | = 460 seconds |
| Gel time at 160° C. after 52 days at room temperature | = 300 seconds |
| Gel time at 160° C. after 52 days at 40° C. | = 90 seconds |

After curing for 2 hours at 160° C. a bond strength under torsion on aluminium of 70 N/mm² is measured.

EXAMPLE 3

180 g (0.1 equivalent) of a diglycidyl ether of so-called "advanced" bisphenol A, prepared, for example, as indicated in Example 1, with an epoxide content of 0.55 equivalent/kg, 55.5 g (0.3 equivalent) of a diglycidyl ether of bisphenol A with an epoxide content of 5.4 equivalents/kg and 108 g (0.6 equivalent) of an epoxyphenol novolac with an epoxide content of 5.56 equivalents/kg are mixed, at 160° C., with 22.8 (0.2 equivalent) of bisphenol A, 99.6 g (0.4 equivalent) of tetrabromobisphenol A and 28.8 g (0.3 equivalent) of the trihydroxy compound of the formula I in which $R_1=R_2=R_3=$hydrogen. 1.0 g (0.2%) of 1-methylimidazole is then mixed in and immediately thereafter the mixture is poured out onto a cold Al sheet. The resulting product is grindable at room temperature and has the following characteristics:

| Glass transition temperature | |
|---|---|
| (DSC-1, 16° C./minute) | = 49° C. |
| Gel time at 160° C. | = 180 seconds |

The cured product is flame-retardant and has the following bond strengths under torsion on aluminium:

| After curing for 30 minutes at 160° C. | = 77 N/mm$^2$ |
|---|---|
| After curing for 2 hours at 140° C. and 2 hours at 210° C. | = 79 N/mm$^2$. |

EXAMPLE 4

182 parts of a higher molecular weight diphenylolpropane diglycidyl ether resin (epoxide content 0.55 equivalent/kg, cf. Example 1) and 180 parts of an epoxide novolac resin which contains 5.56 epoxide equivalents per kg are mixed at room temperature (20° C.). 57 parts of finely ground bisphenol A and 48 parts of a condensation product of phenol and acrolein (formula I, $R_1=R_2=R_3=H$) are then added to the resin mixture. The mixture is warmed at 160° C. until the phenol-containing products have dissolved. 0.2% of a surface-active product based on polysiloxane and also 7 percent by weight of azodicarboxamide are then admixed in a kneader. Finally, 0.9 part of methylimidazole is added to the mixture. The mixture thus obtained is discharged immediately and cooled to room temperature very rapidly using solid carbon dioxide. 18 g of the product are introduced into a steel mould which has dimensions of 64×34×16 mm and has been pre-heated to 150° C. and the mould is closed. After curing for 1 hour, a foamed article with a density of 0.4 g/cm$^3$ is removed from the mould; this product has a very fine pore structure. Its softening temperature is 123° C.

EXAMPLE 5

The following substances are mixed in a kneader, the jacket temperature of which has been set at 70° C.: 55.5 parts of diphenylolpropane diglycidyl ether (epoxide equivalent 5.4), 182 parts of a higher molecular weight diphenylolpropane diglycidyl ether resin (epoxide equivalent 0.55, cf. Example 1), 108 parts of an epoxy novolac with an epoxide equivalent of 5.56, 28.8 parts of a condensation product of phenol and acrolein (formula I, $R_1=R_2=R_3=H$), 22.8 parts of bisphenol A, 100 parts of tetrabromobisphenol A, 1 part of 1-methylimidazole, 0.2% of a surfactant based on polysiloxane and 7% of azodicarboxamide.

The so-called "advancement" in the kneader is continued for 30 minutes. The pasty product is then removed from the kneader and cooled. 18 g of the product, which has been ground in a mill, are introduced into a steel mould which has dimensions of 65×34×16 mm and has been preheated to 160° C. The mould is closed and kept at 160° C. for 1 hour. After curing has taken place and after subsequent cooling, a foamed article with a density of 0.4 g/cm$^3$ is removed from the mould. This article has a fine and homogeneous pore structure. Its softening temperature measured on a TMS apparatus is 120° C.

EXAMPLE 6

135 g (0.75 equivalent) of an epoxide novolac with an epoxide content of 5.56 equivalents/kg and 455 g (0.25 equivalent) of a so-called "advanced" bisphenol A diglycidyl compound with an epoxide content of 0.55 equivalent/kg are mixed, at 140° C., with 21.0 g (0.5 equivalent) of 1,2,3-trihydroxybenzene and 57.0 g (0.5 equivalent) of bisphenol A. 0.67 g (0.1%) of 2-phenylimidazole is mixed in and the mixture is then immediately poured out onto a Al sheet. The resulting product is grindable and has the following characteristics:

| Glass transition temperature (DSC, 16° C./minute) | = 41° C. |
|---|---|
| Gel time at 160° C. | = 10 minutes |
| After curing the mixture, the following bond strengths under torsion on aluminium are measured: | |
| Curing for 15 minutes at 160° C. | = 39 N/mm$^2$ |
| Curing for 60 minutes at 160° C. | = 81 N/mm$^2$ |

EXAMPLE 7

52.5 g (0.3 equivalent) of an epoxide novolac with an epoxide content of 5.7 equivalents/kg, 364 g (0.4 equivalent) of a so-called "advanced" bisphenol A diglycidyl compound with an epoxide content of 1.1 equivalents/kg and 93.7 g (0.3 equivalent) of a brominated bisphenol A diglycidyl compound with an epoxide content of 3.2 equivalents/kg are mixed, at 160° C., with 149.4 g (0.6 equivalent) of tetrabromobisphenol A and 16.8 g (0.4 equivalent) of 1,2,3-trihydroxybenzene. 3.4 g (0.5%) of a compound having the following constitution $NC(CH_2)_2NH(CH_2)_3N(CH_3)_2$ are mixed in, after which the mixture is immediately poured out onto a Al sheet. The resulting product is grindable and has the following characteristics:

| Glass transition temperature (DSC, 16° C./minute) | = 45° C. |
|---|---|
| Gel time at 160° C. | = 10 minutes |

After curing the mixture, the following bond strengths under torsion on aluminium are measured:

| Curing for 15 minutes at 160° C. | = 33 N/mm$^2$ |
|---|---|
| Curing for 60 minutes at 160° C. | = 78 N/mm$^2$ |

EXAMPLE 8

364 g (0.4 equivalent) of a so-called "advanced" bisphenol A diglycidyl compound with an epoxide content of 1.1 equivalents/kg and 100 g (0.6 equivalent) of a hydantoin compound which has the following constitution

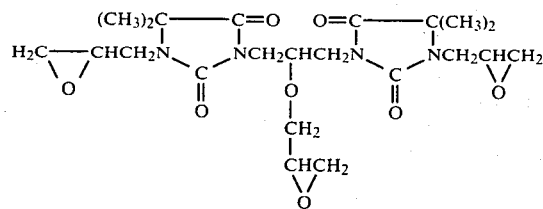

and an epoxide content of 6.0 equivalents/kg are mixed, at 140° C., with 24.8 g (0.4 equivalent) of 2,6-dihydroxytoluene and 57.6 g (0.6 equivalent) of 1,1,3-tris(hydroxyphenyl)-propane. 2.7 g (0.05%) of a 10% aqueous solution of tetramethylammonium chloride are mixed in, after which the mixture is immediately poured out onto a Al sheet. The resulting product is grindable and has the following characteristics:

| | |
|---|---|
| Glass transition temperature (DSC, 16° C./minute) | = 52°C. |
| Gel time at 160° C. | = 10 minutes |

After curing the mixture, the following bond strengths under torsion on aluminium are measured:

| | |
|---|---|
| Curing for 15 minutes at 160° C. | = 29 N/mm² |
| Curing for 60 minutes at 160° C. | = 85 N/mm² |

EXAMPLE 9

546 g (0.6 equivalent) of a so-called "advanced" bisphenol A diglycidyl compound with an epoxide content of 1.1 equivalents/kg, 546 g (3.26 equivalents) of a hydantoin triglycidyl compound corresponding to Example 8, 76.8 g (0.8 equivalent) of tris-(hydroxyphenyl)-propane, 24.8 g (0.4 equivalent) of 2,6-dihydroxytoluene, 147.4 g (2.68 equivalents) of 1,3-dihydroxybenzene, 2.7 g (0.2%) of Aerosil 200 (Degussa) and 10.0 g (0.1%) of tetramethylammonium chloride (10% aqueous solution) are added together and melted at 140° C. The mixture is poured onto a Al sheet and allowed to cool. The resulting glassy mass is grindable and has the following characteristics:

| | |
|---|---|
| Glass transition temperature (DSC, 16° C./minute) | = 44° C. |
| Gel time at 160° C. | = 6½ minutes |
| Gel time at 180° C. | = 3½ minutes |
| Bond strength under torsion on Al after curing for 1 hour at 160° C. | = 68 N/mm² |
| Bond strength under torsion on Al after curing for 2 hours at 160° C. | = 81 N/mm² |

What is claimed is:

1. A storable, solid mixture for the preparation of a plastic which is based on epoxide resin and is stable to hydrolysis, which comprises (a) a long-chain, linear epoxide resin, which is free from ester groups, is solid at room temperature and has an epoxide equivalent weight of >700; (b) a compound which is free from ester groups, contains cyclic structures and 2 or 3 epoxide groups in the molecule and has an epoxide equivalent weight of 100 to 400, the components (a) and (b) being present in a ratio such that, per 1 total epoxide equivalent, 0.05 to 0.3 equivalent originates from (a) and 0.7 to 0.95 equivalent originates from (b); (c) the condensation product of 3 mols of phenol and 1 mol of acrolein, in an amount such that there are 0.5 to 1.1 equivalents of the phenolic hydroxy compound per epoxide equivalent with 0 to 70 equivalent % of said product being replaced by a phenolic bis-hydroxy compound; and (d) a curing accelerator.

2. A mixture according to claim 1, which contains components (a) and (b) in a ratio such that, per 1 epoxide equivalent, 0.05 to 0.2 equivalent originates from (a) and 0.8 to 0.95 equivalent originates from (b).

3. A mixture according to claim 1, which contains, as component (c), a trisphenol of the formula I

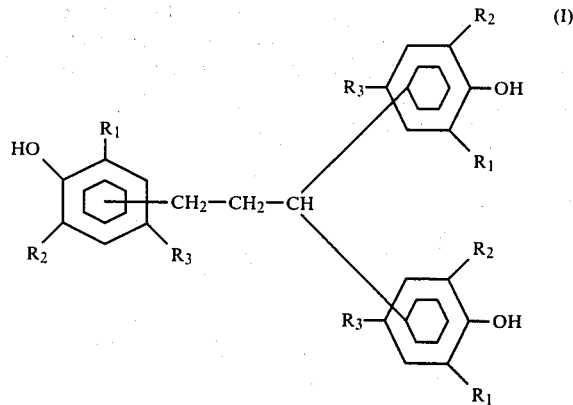

in which R₁ and R₂ are hydrogen, and R₃ is hydrogen.

4. A mixture according to claim 1, which contains, as component (a), a diglycidyl compound with an epoxide equivalent weight of >1,000.

5. A mixture according to claim 1, which contains, as component (b), a di- or tri-epoxide compound with an epoxide equivalent weight of 150 to 300.

6. A mixture according to claim 5, which contains, as component (b), the diglycidyl ether of bisphenol A or F.

7. A mixture according to claim 5, which contains, as component (b), an epoxyphenol novolac or epoxycresol novolac.

8. A mixture according to claim 5, which contains, as component (b), triglycidyl isocyanurate or a di- or triglycidyl derivative of a hydantoin.

9. A mixture according to claim 1, which contains, as component (d), a tertiary amine, an imidazole, an alkali metal alcoholate or a quaternary ammonium salt.

10. A mixture according to claim 1, which contains, as component (a), a diglycidyl ether of an advanced bisphenol A, with an epoxide content of 0.5 equivalent/kg, as component (b) an epoxide novolac with an epoxide content of 5.6 equivalents/kg, the components (a) and (b) being present in a ratio such that, per 1 epoxide equivalent, 0.1 equivalent originates from (a) and 0.9 equivalent originates from (b), as component (c), 1,1,3-tris-(hydroxyphenyl)-propane and bisphenol A in a ratio such that, per 1 epoxide equivalent, 0.5 equivalent of the phenolic hydroxy groups originates from 1,1,3-tris-(hydroxyphenyl)-propane and 0.5 equivalent originates from bisphenol A, and, as component (d), 1-methylimidazole.

11. A mixture according to claim 1, which additionally contains a blowing agent.

12. A plastic which is based on epoxide resin and has been prepared from a mixture according to claim 1.

13. A plastic prepared from a mixture according to claim 1 by allowing said mixture to react at a temperature of more than 120° C.

* * * * *